US00PP28683P3

(12) United States Plant Patent
Beekenkamp

(10) Patent No.: US PP28,683 P3
(45) Date of Patent: Nov. 21, 2017

(54) ***BEGONIA* PLANT NAMED 'BKPBEWFASO'**

(50) Latin Name: *Begonia pendula*
Varietal Denomination: BKPBEWFASO

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 34 days.

(21) Appl. No.: 14/756,923

(22) Filed: Oct. 30, 2015

(65) Prior Publication Data

US 2017/0127592 P1 May 4, 2017

(51) Int. Cl.
*A01H 5/02* (2006.01)

(52) U.S. Cl.
USPC ..... Plt./347

(58) Field of Classification Search
USPC ..... Plt./347
See application file for complete search history.

*Primary Examiner* — Keith Robinson
(74) *Attorney, Agent, or Firm* — C. A. Whealy

(57) ABSTRACT

A new and distinct cultivar of *Begonia* plant named 'BKPBEWFASO', characterized by its upright to broadly outwardly spreading and eventually hanging plant habit; freely branching habit; dark green-colored leaves; freely flowering habit and long flowering period; large salmon and light yellowish pink-colored flowers; and good garden performance.

2 Drawing Sheets

Botanical designation: *Begonia pendula.*
Cultivar denomination: 'BKPBEWFASO'.

BACKGROUND OF THE INVENTION

The present invention relates to a new and distinct cultivar of *Begonia* plant, botanically known as *Begonia pendula* and hereinafter referred to by the name 'BKPBEWFASO'.

The new *Begonia* plant is a product of a planned breeding program conducted by the Inventor in Maasdijk, The Netherlands. The objective of the breeding program was to develop new freely flowering *Begonia* plants with large attractive flowers and good garden performance.

The new *Begonia* plant originated from a cross-pollination made by the Inventor in January, 2011 of a proprietary selection of *Begonia pendula* identified as code number 03-H28, not patented, as the female, or seed, parent with a proprietary selection of *Begonia pendula* identified as code number 10-000-29, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in July, 2011.

Asexual reproduction of the new *Begonia* plant by vegetative tip cuttings in a controlled greenhouse environment in Maasdijk, The Netherlands since August, 2012 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEWFASO'. These characteristics in combination distinguish 'BKPBEWFASO' as a new and distinct *Begonia* plant:

1. Upright to broadly outwardly spreading and eventually hanging plant habit.
2. Freely branching habit.
3. Dark green-colored leaves.
4. Freely flowering habit and long flowering period.
5. Large salmon and light yellowish pink-colored flowers.
6. Good garden performance.

Plants of the new *Begonia* can be compared to plants of the female parent selection. Plants of the new *Begonia* differ primarily from plants of the female parent selection in the following characteristics:

1. Plants of the new *Begonia* have single and semi-double flowers whereas plants of the female parent selection have double flowers.
2. Plants of the new *Begonia* have salmon and light yellowish pink-colored flowers whereas plants of the female parent selection have bright orange-colored flowers.

Plants of the new *Begonia* can be compared to plants of the male parent selection. Plants of the new *Begonia* differ primarily from plants of the male parent selection in the following characteristics:

1. Plants of the new *Begonia* are not as compact as plants of the male parent selection.
2. Plants of the new *Begonia* have larger flowers than plants of the male parent selection.
3. Plants of the new *Begonia* have salmon and light yellowish pink-colored flowers whereas plants of the male parent selection have pink and white-colored flowers.

Plants of the new *Begonia* can be compared to plants of the *Begonia pendula* 'BKBEWFAFSP', disclosed in U.S. Plant Pat. No. 24,304. In side-by-side comparisons conducted in Maasdijk, The Netherlands, plants of the new *Begonia* differ from plants of 'BKBEWFAFSP' in the following characteristics:

1. Plants of the new *Begonia* have slightly larger flowers than plants of 'BKBEWFAFSP'.
2. Plants of the new *Begonia* have salmon and light yellowish pink-colored flowers whereas plants of 'BKBEWFAFSP' have light and dark pink-colored flowers.

Plants of the new *Begonia* can also be compared to plants of the *Begonia* 'Dainty Dancer Apricot', not patented. In side-by-side comparisons conducted in Maasdijk, The Netherlands, plants of the new *Begonia* differ from plants of 'Dainty Dancer Apricot' in the following characteristics:

1. Plants of the new *Begonia* are not as freely branching as plants of 'Dainty Dancer Apricot'.
2. Plants of the new *Begonia* have larger flowers than plants of 'Dainty Dancer Apricot'.
3. Plants of the new *Begonia* have salmon and light yellowish pink-colored flowers whereas plants of 'Dainty Dancer Apricot' have apricot-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEWFASO' grown in a container.

The photograph on the second sheet are close-up views of upper and lower surfaces of typical flowers and leaves of 'BKPBEWFASO' and at the bottom center of the photograph is a close-up view of typical flower buds and opening flowers with pedicels.

DETAILED BOTANICAL DESCRIPTION

Plants used for the aforementioned photographs and following observations and measurements were grown in 12-cm containers during the winter in a glass-covered greenhouse in Maasdijk, The Netherlands. During the production of the plants, day temperatures ranged from 19° to 20° C., night temperatures ranged from 18° to 19° C. and light levels averaged 6,000 lux. Plants were eight weeks old when the photographs and the description were taken. In the following description, color references are made to The Royal Horticultural Society Colour Chart, 2007 Edition, except where general terms of ordinary dictionary significance are used.

Botanical classification: *Begonia pendula 'BKPBEWFASO'*.

Parentage:

*Female, or seed, parent.*—Proprietary selection of *Begonia pendula* identified as code number 03-H28, not patented.

*Male, or pollen, parent.*—Proprietary selection of *Begonia pendula* identified as code number 10-000-29, not patented.

Propagation:

*Type.*—By vegetative tip cuttings.

*Time to initiate roots, summer.*—About one week at temperatures about 20° C. to 25° C.

*Time to initiate roots, winter.*—About one week at temperatures about 18° C. to 20° C.

*Time to produce a rooted young plant, summer.*—About 32 days at temperatures about 20° C. to 25° C.

*Time to produce a rooted young plant, winter.*—About 35 days at temperatures about 18° C. to 20° C.

*Root description.*—Medium in thickness, fibrous; typically white in color, actual color of the roots is dependent on substrate composition, water quality, fertilizer type and formulation, substrate temperature and physiological age of roots; plants of the new *Begonia* have not been observed to form tubers.

*Rooting habit.*—Moderate freely branching; medium density.

Plant description:

*Plant and growth habit.*—Upright to broadly outwardly spreading and eventually hanging plant habit; plant shape roughly flattened globular; freely branching habit with about nine basal and lateral branches developing per plant; moderately vigorous growth habit and moderate growth rate.

*Plant height.*—About 15.5 cm.

*Plant width.*—About 32.6 cm.

*Lateral branch description.*—Length: About 5.8 cm. Diameter: About 7 mm. Internode length: About 1.3 cm. Strength: Moderately weak, bending with the weight of the leaves and flowers. Aspect: About 50° from the vertical and main stem axis. Texture: Sparsely pubescent. Luster: Slightly glossy. Color, developing: Close to 152D. Color, fully developed: Close to between 148A and 152B.

*Leaf description.*—Arrangement: Alternate, simple. Length: About 12.2 cm. Width: About 5.4 cm. Shape: Ovate to narrowly ovate. Apex: Acute. Base: Unequal, hastate; lobes not imbricate to imbricate. Margin: Biserrate. Texture, upper and lower surfaces: Sparsely pubescent; velvety. Luster, upper surface: Very slightly glossy. Luster, lower surface: Matte. Venation pattern: Laciniate. Color: Developing leaves, upper surface: Close to between 152A and N199A. Developing leaves, lower surface: Close to 176A. Fully expanded leaves, upper surface: Much darker than N189A; venation, close to 146A to 146B. Fully expanded leaves, lower surface: Close to 183B; venation, close to 148B. Petioles: Length: About 3.4 cm. Diameter: About 3.5 mm. Texture, upper and lower surfaces: Pubescent. Luster, upper and lower surfaces: Glossy. Color, upper surface: Close to 176A; distally, close to 183A. Color, lower surface: Close to 177B to 177C. Stipules: Quantity per leaf: Two. Length: About 6 mm. Width: About 4 mm. Shape: Ovate. Apex: Broadly acute. Base: Broadly cuneate. Margins: Entire. Color, upper and lower surfaces: Close to 145D; towards the margins, 185B; venation, close to 185B.

Flower description:

*Flowering habit.*—Cruciform single male flowers and rotate single female flowers; flowers arranged in axillary cymes; freely flowering habit with about two to three flowers per cyme and about 144 flowers developing per plant; flowers face outwardly to slightly drooping.

*Fragrance.*—None detected.

*Natural flowering season.*—Plants begin flowering about 45 days after planting; long flowering period, plants flower freely and continuously from spring into the autumn in The Netherlands.

*Postproduction longevity.*—Individual flowers last about ten days on the plant; flowers not persistent; plants maintain good substance for about 100 days.

*Inflorescence height.*—About 16.6 cm.

*Inflorescence diameter.*—About 11 cm.

*Flower buds.*—Length: About 3 cm. Diameter: About 1 cm to 3 cm. Shape: Broadly obovate to nearly circular; flattened. Color: Close to 41C to 41D; towards the margins, close to 43C; towards the base, close to 145D.

*Male flowers.*—Diameter: About 8.5 cm. Depth: About 1.9 cm. Tepals: Quantity per flower and arrangement: Four in opposite pairs. Length, pair of broader tepals: About 4.6 cm. Width, pair of broader tepals: About 4.5 cm. Length, pair of narrower tepals: About 4.2 cm. Width, pair of narrower tepals: About 2.2 cm. Shape, pair of broader tepals: Roughly orbicular. Shape, pair of narrower tepals: Narrowly obovate. Apex, all tepals: Obtuse. Margin, all tepals: Entire. Texture, upper surface: Smooth, glabrous; moderately velvety. Texture, lower surface: Smooth, glabrous; slightly velvety. Luster, upper surface: Matte. Luster, lower surface: Slightly glossy. Color: When opening, upper surface: Close to 4D; towards the margins, tinged with close to 37B. When opening, lower surface: Close to 41C to 41D. Fully opened, upper surface: Close to 4D, slightly to moderately tinged with close to 37C to 37D; towards the margins of the pair of broader tepals, close to 41B to 41C; color does not fade with development. Fully opened, lower surface: Close to 4D, moderately tinged with close to 38A; towards the margins of the pair of broader tepals, close to 41B to 41C; color does not fade with development. Tepaloids: None observed on male flowers.

*Female flowers.*—Diameter: About 6.9 cm. Depth: About 1.5 cm. Tepals: Quantity per flower and arrangement: Five, arranged in a single whorl. Length: About 3.5 cm. Width: About 2.7 cm. Shape: Obovate. Apex: Obtuse. Margin: Entire. Texture, upper surface: Smooth, glabrous; moderately velvety. Texture, lower surface: Smooth, glabrous; slightly velvety. Luster, upper surface: Matte. Luster, lower surface: Slightly glossy. Color: When opening, upper surface: Close to 4D; towards the margins, tinged with close to 37B. When opening, lower surface: Close to 41C to 41D. Fully opened, upper surface: Close to 4D, slightly to moderately tinged with close to 37C to 37D; color does not fade with development. Fully opened, lower surface: Close to 4D, moderately tinged with close to 38A; color does not fade with development. Tepaloids: None observed on female flowers.

*Peduncles, male and female flowers.*—Length: About 7.6 cm. Diameter: About 4 mm. Angle: About 60° from lateral branch axis. Strength: Moderately strong; flexible and bending with the weight of the flowers. Texture: Very sparsely pubescent. Luster: Moderately glossy. Color, upper surface: Close to 175D; distally, close to 172A. Color, lower surface: Close to 177B to 177C.

*Pedicels, male and female flowers.*—Length: About 5 cm. Diameter: About 2.5 mm. Angle: Female flowers, about 20° to 50° from the peduncle axis; male flowers typically directly beyond peduncle. Strength: Moderately strong; flexible, bending with the weight of the flowers. Texture: Smooth, glabrous. Luster: Moderately glossy. Color, upper surface: Close to 179A. Color, lower surface: Close to between 174D and 199D.

*Flower bracts.*—Quantity per flower: Two. Length: About 1.6 cm. Width: About 1.7 cm. Shape: Roughly orbicular. Margin: Entire. Texture, upper and lower surfaces: Smooth, glabrous; velvety. Luster, upper and lower surfaces: Moderately glossy. Color, upper and lower surfaces: Close to 145A to 145B.

*Reproductive organs.*—Androecium: Present only on male flowers. Stamen quantity per flower: About 80. Filament length: About 8 mm. Anther length: About 2 mm. Anther shape: Club-shaped. Anther color: Close to 17B. Amount of pollen: Moderate. Pollen color: Close to 1C. Gynoecium: Present only on female flowers. Quantity per flower: Six, fused in pairs. Pistil length: About 9 mm. Stigma shape: Spiral. Stigma color: Close to 17C. Style length: About 7 mm. Style color: Close to 13B. Ovary color: Close to 145C strongly tinged with close to 179A to 179B. Seeds and fruits: Seed and fruit development have not been observed on plants of the new *Begonia*.

Disease & pest resistance: Resistance to pathogens and pests common to *Begonia* plants has not been observed on plants of the new *Begonia*.

Garden performance & temperature tolerance: Plants of the new *Begonia* have been observed to have good garden performance, to tolerate high temperatures of about 35° C. and to be hardy to USDA Hardiness Zone 10.

It is claimed:

1. A new and distinct *Begonia* plant named 'BKPBEWFASO' as illustrated and described.

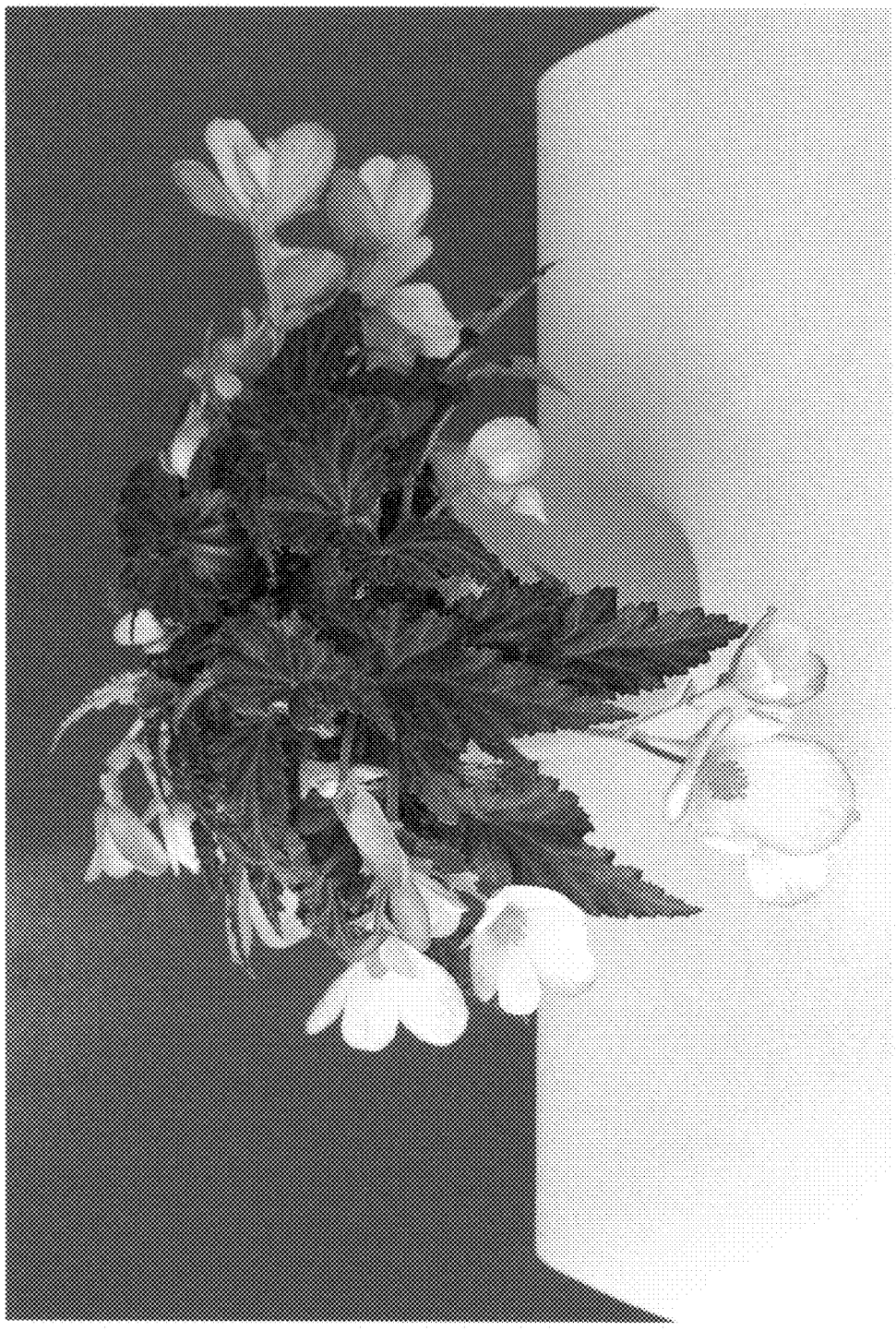

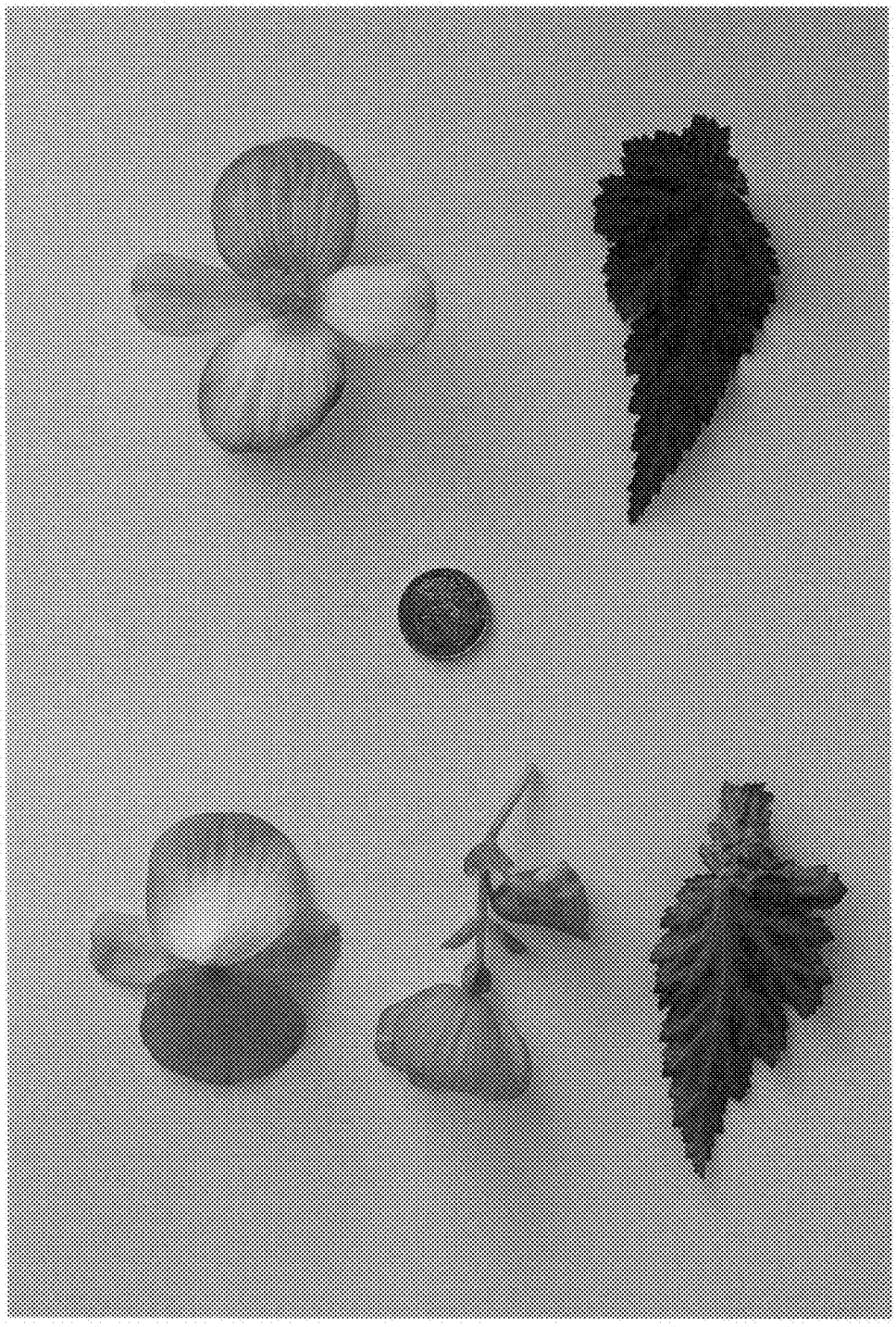

* * * * *